US012702733B2

(12) United States Patent
Pouchoulin et al.

(10) Patent No.: US 12,702,733 B2
(45) Date of Patent: Aug. 11, 2026

(54) APPARATUS FOR EXTRACORPOREAL BLOOD TREATMENT AND METHOD FOR CALCULATING CALORIC BALANCE IN AN APPARATUS FOR EXTRACORPOREAL BLOOD TREATMENT

(71) Applicant: GAMBRO LUNDIA AB, Lund (SE)

(72) Inventors: Dominique Pouchoulin, Tramoyes (FR); Viktoria Roos, Eslöv (SE)

(73) Assignee: Gambro Lundia AB, Lund (SE)

( * ) Notice: Subject to any disclaimer, the term of this patent is extended or adjusted under 35 U.S.C. 154(b) by 366 days.

(21) Appl. No.: 18/570,696

(22) PCT Filed: May 25, 2022

(86) PCT No.: PCT/EP2022/064329

§ 371 (c)(1),
(2) Date: Dec. 15, 2023

(87) PCT Pub. No.: WO2022/268432

PCT Pub. Date: Dec. 29, 2022

(65) Prior Publication Data

US 2025/0041494 A1 Feb. 6, 2025

(30) Foreign Application Priority Data

Jun. 22, 2021 (EP) .................................... 21180794

(51) Int. Cl.
*A61M 60/37* (2021.01)
*A61M 1/16* (2006.01)
(Continued)

(52) U.S. Cl.
CPC ............ *A61M 1/1607* (2014.02); *A61M 1/16* (2013.01); *A61M 1/1609* (2014.02); *A61M 1/34* (2013.01);
(Continued)

(58) Field of Classification Search
CPC ........ A61M 1/16; A61M 1/1607; A61M 1/34; A61M 1/3413; A61M 1/342;
(Continued)

(56) References Cited

U.S. PATENT DOCUMENTS 4,378,797 A 4/1983 Osterholm
4,726,381 A 2/1988 Jones
(Continued)

FOREIGN PATENT DOCUMENTS

DE 202016002935 5/2016
EP 0986410 3/2006
(Continued)

OTHER PUBLICATIONS

Fiaccadori et al, "ESPEN Guideline on Clinical Nutrition in Hospitalized Patients with Acute or Chronic Kidney Disease," Clinical Nutrition 40 (2021) 1644-1668.
(Continued)

*Primary Examiner* — John Kim
(74) *Attorney, Agent, or Firm* — Mueting Raasch Group

(57) ABSTRACT

An apparatus for extracorporeal blood treatment comprises a control unit (100) which, during the extracorporeal blood treatment, is programmed for: computing a mass balance rate ($J_{soln}$) of a selected solute or solutes from a solute concentration ($C_{soln}$) in dialysis fluid and/or infusion fluids, from a patient solute concentration ($Cp_{soln}$), from a fluid flow rate or rates (Qpbp, Qpre, Qpost, Qdial, Qanc) and from a filtration flow rate (Qfil) or a patient fluid removal rate (Qpfr); computing, from the computed mass balance rate ($J_{soln}$) and from a specific energy load ($Emet_{soln}$) of each solute, an energy balance ($E_{soln}$) due to the selected solute or solutes.

26 Claims, 2 Drawing Sheets

(51) Int. Cl.

| | |
|---|---|
| ***A61M 1/34*** | (2006.01) |
| ***A61M 1/36*** | (2006.01) |
| ***A61M 60/113*** | (2021.01) |
| ***A61M 60/279*** | (2021.01) |
| ***G16H 20/17*** | (2018.01) |
| ***G16H 20/40*** | (2018.01) |

(52) U.S. Cl.
CPC .......... *A61M 1/3413* (2013.01); *A61M 1/342* (2013.01); *A61M 1/3672* (2013.01); *A61M 60/113* (2021.01); *A61M 60/279* (2021.01); *A61M 60/37* (2021.01); *G16H 20/17* (2018.01); *G16H 20/40* (2018.01); *A61M 2205/3334* (2013.01); *A61M 2205/50* (2013.01); *A61M 2205/502* (2013.01); *A61M 2205/583* (2013.01); *A61M 2230/201* (2013.01)

(58) Field of Classification Search
CPC .............. A61M 1/3672; A61M 60/113; A61M 60/279; A61M 60/37; A61M 2205/3334; A61M 2205/50; A61M 2205/502; A61M 2205/583; A61M 2230/201; G16H 20/17; G16H 20/40
See application file for complete search history.

(56) References Cited

U.S. PATENT DOCUMENTS

| | | | | |
|---|---|---|---|---|
| 4,731,731 | A | 3/1988 | Cochran | |
| 4,739,492 | A | 4/1988 | Cochran | |
| 9,463,266 | B2 | 10/2016 | Noguchi | |
| 2008/0026391 | A1 | 1/2008 | Ichiishi | |
| 2010/0096330 | A1 | 4/2010 | Gotch | |
| 2010/0112583 | A1 | 5/2010 | Ichiishi | |
| 2013/0134077 | A1 | 5/2013 | Wieskotten | |
| 2017/0045455 | A1 | 2/2017 | Robertson | |
| 2018/0353670 | A1 | 12/2018 | Kommala | |
| 2019/0201607 | A1 | 7/2019 | Oberg | |
| 2024/0016989 | A1 * | 1/2024 | Pouchoulin ......... | A61M 1/1603 |

FOREIGN PATENT DOCUMENTS

| | | |
|---|---|---|
| EP | 2345893 | 5/2016 |
| EP | 2331165 | 11/2017 |
| EP | 3272347 | 1/2018 |
| JP | 2001337998 | 12/2001 |
| WO | 2009/016504 | 2/2009 |

OTHER PUBLICATIONS

Extended European Search Report for Application No. 21180794.6 dated Dec. 14, 2021 (7 pages).
International Search Report and Written Opinion for PCT/EP2022/064329 dated Sep. 5, 2022 (15 pages).

* cited by examiner 1
2
3
3a
3b
4
4a
4b
5
6
7
8
9
10
11
12
13
14
15
16
17
18
19
20
21
22
23
24
25
26
27
28
100
110
120
130
131
132
133
P

FIG.2

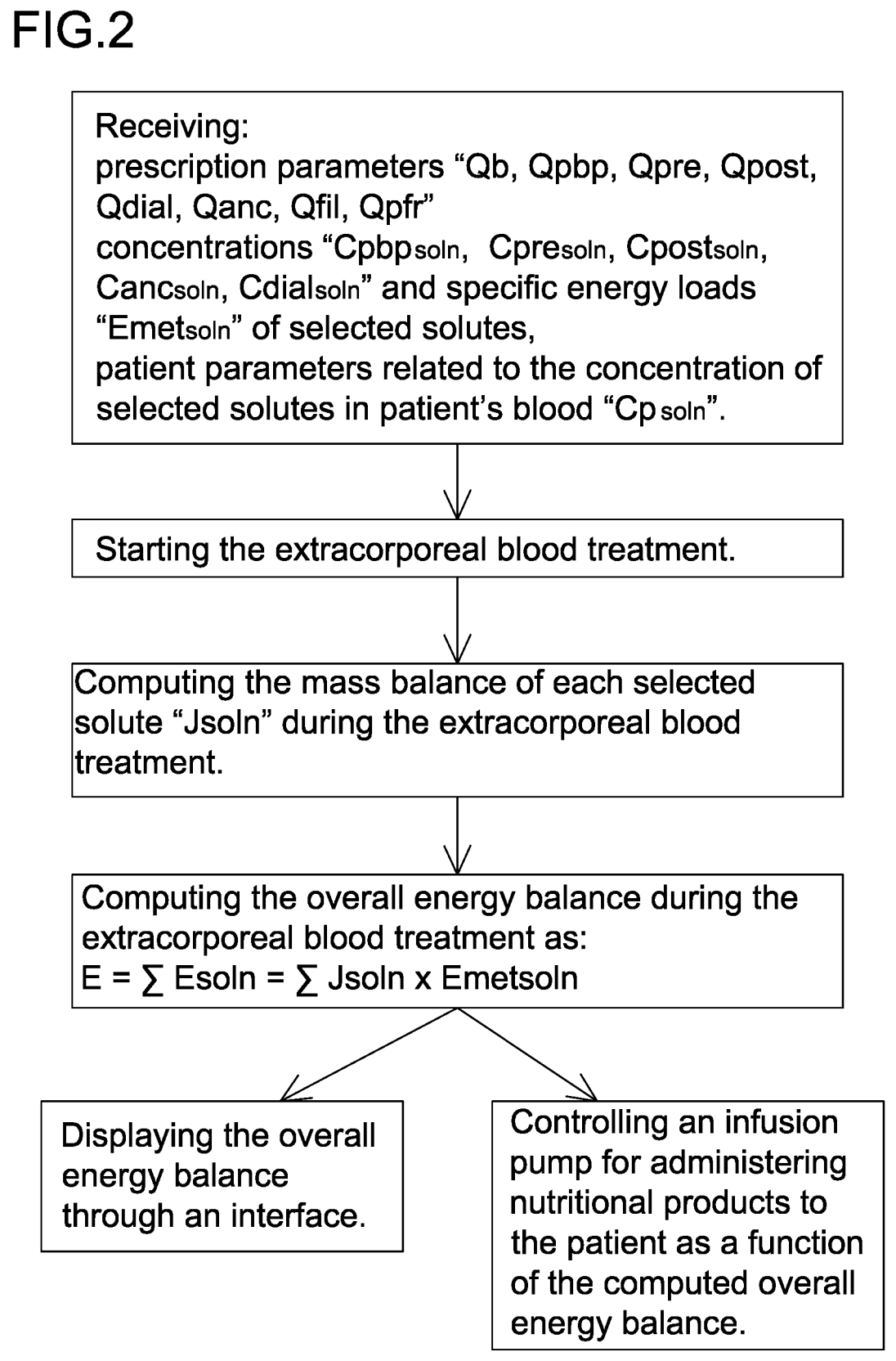

Receiving:
prescription parameters "Qb, Qpbp, Qpre, Qpost, Qdial, Qanc, Qfil, Qpfr"
concentrations "$Cpbp_{soln}$, $Cpre_{soln}$, $Cpost_{soln}$, $Canc_{soln}$, $Cdial_{soln}$" and specific energy loads "$Emet_{soln}$" of selected solutes,
patient parameters related to the concentration of selected solutes in patient's blood "$Cp_{soln}$".

Starting the extracorporeal blood treatment.

Computing the mass balance of each selected solute "Jsoln" during the extracorporeal blood treatment.

Computing the overall energy balance during the extracorporeal blood treatment as:
$E = \sum Esoln = \sum Jsoln \times Emetsoln$ Displaying the overall energy balance through an interface.

Controlling an infusion pump for administering nutritional products to the patient as a function of the computed overall energy balance.

APPARATUS FOR EXTRACORPOREAL BLOOD TREATMENT AND METHOD FOR CALCULATING CALORIC BALANCE IN AN APPARATUS FOR EXTRACORPOREAL BLOOD TREATMENT

This application is a U.S. National Stage Application of International Application No. PCT/EP2022/064329 filed May 25, 2022, which was published in English on Dec. 29, 2022, as International Publication No. WO 2022/268432 A1. International Application No. PCT/EP2022/064329 claims priority to European Application No. 21180794.6 filed Jun. 22, 2021.

TECHNICAL FIELD

The present invention relates to an apparatus for extracorporeal blood treatment and to a method for calculating caloric balance.

Extracorporeal blood treatment involves removing blood from a patient, treating the blood externally to the patient, and returning the treated blood to the patient. Extracorporeal blood treatment is typically used to extract undesirable matter or molecules from the patient's blood and add desirable matter or molecules to the blood. Extracorporeal blood treatment is used with patients unable to effectively remove matter from their blood, such as when a patient has suffered temporary or permanent kidney failure. These patients and other patients may undergo extracorporeal blood treatment to add or remove matter to their blood, to maintain an acid/base balance, to remove excess body fluids or to perform extracorporeal gas exchange processes, for example.

The invention mainly refers to continuous renal replacement therapy (CRRT) systems. CRRT systems are configured for delivering treatments designed for patients versing in acute states of illness and who have temporarily lost their kidney function in its entirety. CRRT monitors should be able to deliver various therapies (SCUF, CCVH, CVVHDF).

BACKGROUND OF THE INVENTION

During extracorporeal blood treatments, the exchange of matters between the apparatus for extracorporeal blood treatment and the patient implies also exchange of energy/caloric load. Said energy/caloric load is due to solutes in the therapy fluids. The therapy fluids are a potential source of said calories that is poorly recognized and may contribute to overfeeding or underfeeding complications.

For instance, the continuous renal replacement therapy (CRRT) treatment contributes to the energy uptake by providing glucose and citrate to the patient, in particular during Regional Citrate Anticoagulation (RCA). When citrate above physiological levels are infused into the patient, the treatment contributes to a substantial amount of energy. Document New et al. ("Continuous renal replacement therapy: a potential source of calories in the critically ill." Am J Clin Nutr 2017; 105:1559-63) discloses that, during Continuous Veno-Venous Hemofiltration (CVVH), the caloric load of citrate and glucose (when applying Anticoagulant Citrate Dextrose Solution, Solution A (ACD-A)) has been estimated to over 500 kcal/day, equivalent to about 30% of the daily energy requirements of the patient. With ACD-A together with high lactate replacement fluids, the CRRT treatment may provide more than 1300 kcal/day.

Excessive energy uptake (overfeeding) is associated with multiple complications in critically ill patients, including hypercapnia, hepatic dysfunction, azotemia, altered immune function and hyperglycemia, and may be also associated with increased mortality in patients in Intensive Care Units (ICU).

Nowadays, when extracorporeal blood treatments are performed, said energy/caloric load due to the solutes in therapy fluids is not taken into account and may contribute to the above mentioned overfeeding complications.

An aim of the present invention is to provide for an apparatus for extracorporeal blood treatment that alleviates or minimizes or remedy the above-mentioned drawback.

It is an aim of the present invention to provide a better energy balance (load or loss) to the patients during extracorporeal blood treatments.

It is an aim of the present invention to avoid overfeeding during the extracorporeal blood treatments.

It is an aim of the present invention to reduce risks of criticalities in patients undergoing treatment, in particular to reduce multiple complications in critically ill patients and to improve outcome for the critically ill patients.

It is a further aim of the present invention to improve the staff awareness of the fact that the treatment provides calories to the patient.

It is a further aim of the present invention to improve the comfort of patients undergoing treatment.

It is a further aim of the present invention to reduce the workload of the clinical staff.

SUMMARY

An apparatus according to one or more of the appended claims, taken singly or in any combination, attains at least one of the above-indicated aims.

The present invention provides an extracorporeal blood treatment apparatus and a method which are able to evaluate, during the treatment, the exchange of energy/caloric load to/from the patient due to at least one of the solutes in the therapy fluid/s.

An apparatus and a method according to aspects of the invention and capable of achieving one or more of the above aims are here below described.

In a $1^{st}$ independent aspect there is provided an apparatus for extracorporeal blood treatment, comprising:

- a blood circuit coupled to the treatment unit and comprising a blood removal line and a blood return line connectable to a vascular system of a patient;
- a blood pump configured to be coupled to a pump section of the blood circuit;
- an effluent line connected to the treatment unit;
- at least one infusion line connected to the blood circuit and/or a dialysis line connected to the treatment unit;
- wherein the at least one infusion line and the dialysis line are connected or connectable to at least one source of at least one fluid;
- a control unit connected at least to the blood pump and programmed for receiving:
  - a solute concentration of at least one selected solute in the at least one fluid;
  - at least one patient parameter related to a patient solute concentration of the at least one selected solute
  - in patient's blood; optionally, the patient parameter being the patient solute concentration;
  - a specific energy load of the at least one selected solute;
  - a measured or set fluid flow rate or rates of the at least one fluid crossing the at least one infusion line and/or the dialysis line;

a measured or set filtration flow rate in the treatment unit or a measured or set patient fluid removal rate.

During the extracorporeal blood treatment, the control unit being programmed for:

computing a mass balance rate of the at least one selected solute from the solute concentration, from the patient parameter, from the fluid flow rate or rates and from the filtration flow rate or the patient fluid removal rate;

computing, from the computed mass balance rate and from the specific energy load, an energy balance due to the at least one selected solute during the extracorporeal blood treatment.

Optionally, the control unit is programmed for receiving a blood flow rate through the blood circuit.

Optionally, the extracorporeal blood treatment is programmed for computing the energy balance also from the blood flow rate.

In a $2^{nd}$ independent aspect there is provided a method for calculating caloric balance in an apparatus for extracorporeal blood treatment, wherein the method comprises:

taking into considerations:

a solute concentration of at least one selected solute in at least one fluid crossing at least one infusion line and/or a dialysis line of an apparatus for extracorporeal blood treatment;

at least one patient parameter related to a patient solute concentration of the at least one selected solute in patient's blood; optionally the patient parameter being the patient solute concentration;

a specific energy load of the at least one selected solute;

a measured or set fluid flow rate or rates of the at least one fluid in the at least one infusion line and/or in the dialysis line;

a measured or set filtration flow rate in a treatment unit or a measured or set patient fluid removal rate of the apparatus for extracorporeal blood treatment;

computing, during the extracorporeal blood treatment:

a mass balance rate of the at least one selected solute from the solute concentration, from the patient parameter, from the fluid flow rate or rates and from the filtration flow rate or the patient fluid removal rate; and from the computed mass balance rate and from the specific energy load, an energy balance due to the at least one selected solute during the extracorporeal blood treatment.

The concentration of the at least one selected solute in patient's blood may be the plasma concentration or the plasma water concentration or the whole blood concentration.

In a $3^{rd}$ aspect according to aspect 1 or 2, the control unit is connected to an interface and is configured to display, or the method comprises displaying, the computed energy balance through said interface; optionally, the apparatus for extracorporeal blood treatment comprises said interface.

In a 3rd bis aspect according to aspect 1 or 2 or 3, the control unit is connected to an infusion pump for administering nutritional products to the patient and is configured to control, or the method comprises controlling, the infusion pump as a function also of the computed energy balance.

In a $3^{rd}$ ter aspect according to aspect 3 bis, the apparatus comprises or is connected to an administering device configured to administer nutritional products to the patient during the extracorporeal blood treatment; the administering device comprising a nutritional line and the infusion pump coupled to the nutritional line; the nutritional line being in fluid communication with a nutritional bag and with the blood return line and/or directly with the patient.

In a $3^{rd}$ quarter aspect according to aspect 1, 2 or 3, the control unit is connected to a support tool dealing with nutrition aspects (Clinical Decision Support—CDS) installed on a computer; the computer being connected to an administering device configured to administer nutritional products to the patient comprising a nutritional line and an infusion pump coupled to the nutritional line; the support tool being configured to control the infusion pump as a function also of the computed energy balance from the control unit.

In a 4th aspect according to any one of aspects 1 to 3 ter, computing the energy balance comprises: multiplying the mass balance rate of the at least one selected solute for the respective specific energy load to obtain the energy balance of said selected solute.

In a 5th aspect according to any one of aspects 1 to 4, the energy balance is computed using the following equation:

$$E_{soln} = J_{soln} \times Emet_{soln}$$

wherein $E_{soln}$ energy balance of selected solute n;

$J_{soln}$ mass balance rate of selected solute n;

$Emet_{soln}$ specific energy load of selected solute n;

wherein:

$J_{soln}>0$ is for solute added to patient; and $J_{soln}<0$ is for solute removed from the patient.

In a 6th aspect according to any one of aspects 1 to 5, the at least one selected solute comprise a plurality of selected solutes and the control unit is programmed to sum, or the method comprises summing, the energy balance of all the selected solutes to obtain an overall energy balance due to the selected solutes.

In a $7^{th}$ aspect according to aspect 6, computing the energy balance comprises: multiplying the mass balance rate of each selected solute for the respective specific energy load to obtain the energy balance of each selected solute.

In an 8th aspect according to aspect 6 or 7, the overall energy balance is computed using the following equation:

$$E = \sum E_{soln} = \sum J_{soln} \times Emet_{soln}$$

wherein

E overall energy balance;

$E_{soln}$ energy balance of selected solute n;

$J_{soln}$ mass balance rate of selected solute n;

$Emet_{soln}$ specific energy load of selected solute n.

In a 9th aspect according to any one of aspects 1 to 8, the control unit is programmed to compute, or the method comprises computing, the mass balance rate of the at least one selected solute, or of each selected solute, as a difference between a rate of the selected solute entering blood and a rate of the selected solute leaving blood.

In a 10th aspect according to any one of aspects 1 to 9, the mass balance of the at least one selected solute, or of each selected solute, is computed using the following equation:

$$J_{soln} = Jinf_{soln} - Jeff_{soln}$$

wherein $J_{soln}$ mass balance rate of the selected solute n;

$Jinf_{soln}$ rate of the selected solute n entering blood;

$Jeff_{soln}$ rate of the selected solute n leaving blood.

In an 11th aspect according to aspect 9 or 10, the control unit is programmed to compute, or the method comprises computing, the rate of the at least one selected solute, or of each selected solute, entering blood as a function of the fluid flow rate of the at least one fluid crossing the at least one infusion line and of the solute concentration in said at least one fluid.

In a 12th aspect according to any of aspects 9 to 11, the rate of the at least one selected solute, or of each selected solute, entering blood is calculated using the following equation:

$$Jinf_{soln} = Qinf_p \times Cinf_{soln}$$

wherein $Jinf_{soln}$ rate of the selected solute n entering blood;

$Qinf_p$ flow rate of fluid crossing infusion line p;

$Cinfp_{soln}$ concentration of selected solute n in infusion line p.

In a 13th aspect according to any one of previous aspects 1 to 12, the at least one infusion line comprises: a pre-blood pump line and/or a pre-infusion line and/or a post-infusion line and/or at least one ancillary infusion line; optionally, the at least one ancillary infusion line comprises: an anticoagulant solution line like a heparin line or a citrate line and/or a calcium line.

In a 14th aspect according to aspect 13 when according to any one of aspects 9 to 12, the rate of the at least one selected solute, or of each selected solute, entering blood is calculated using the following equation:

$$Jinf_{soln} = Qpbp \times Cpbp_{soln} + Qpre \times Cpre_{soln} + Qpost \times Cpost_{soln} + Qanc \times Canc_{soln}$$

wherein $Jinf_{soln}$ rate of the selected solute n entering blood;

Qpbp flow rate of fluid crossing pre-blood pump line;

Qpre flow rate of fluid crossing pre-infusion line;

Qpost flow rate of fluid crossing post-infusion line;

Qanc flow rate of fluid crossing ancillary line;

$Cpbp_{soln}$ concentration of selected solute n in pre-blood pump line;

$Cpre_{soln}$in concentration of selected solute n in pre-infusion line;

$Cpost_{soln}$ concentration of selected solute n in post-infusion line;

$Canc_{soln}$ concentration of selected solute n in ancillary line.

In a 15th aspect according to any of aspects 9 to 12 and 14 or according to aspect 13 when according to any one of aspects 9 to 12, the control unit is programmed to compute, or the method comprises computing, the rate of the at least one selected solute leaving blood, or of each selected solute leaving blood, as a function of the filtration flow rate and of the patient parameter.

In a 16th aspect according to aspect 15, the control unit is programmed to compute, or the method comprises computing, the rate of the at least one selected solute leaving blood, or of each selected solute leaving blood, as a function of the fluid flow rate of the fluid crossing the dialysis line.

In a 17th aspect according to aspect 15 or 16, the control unit is programmed to compute, or the method comprises computing, the rate of the at least one selected solute leaving blood, or of each selected solute leaving blood, as a function of a clearance of said solute for said treatment unit.

In an 18th aspect according to aspect 17, the control unit is programmed to compute, or the method comprises computing, the clearance from a diffusive mass transfer coefficient of said solute for said treatment unit.

In a 19th aspect according to aspect 18, the control unit is programmed to compute, or the method comprises computing, the clearance as a function of the filtration flow rate, the fluid flow rate of the fluid crossing the dialysis line, a flow rate of blood in the blood circuit and parameters of patient's blood.

In a 20th aspect according to aspect 19, the parameters of patient's blood comprise:

$\alpha_{soln}$ distribution coefficient of solute n between plasma water and red blood cells (RBC);

$\beta kin_{soln}$ empirical parameter defining the fraction of RBC water volume to consider in mass transfer computations for solute n (dependent on solute kinetics across RBC membrane);

Fp plasma water volume fraction;

Frbc intra erythrocyte water volume fraction;

Hct hematocrit.

In a 21st aspect according to any of aspects 17 to 20, the control unit is programmed to compute, or the method comprises computing, the clearance through the following equation:

$$K_{soln} = [(Qwinlet \times Qdial) - (f_{soln} \times (Qwinlet - Qfil) \times (Qdial + Qfil))] / [Qdial - f_{soln} \times (Qwinlet - Qfil)]$$

wherein $$f_{soln} = \left[((Qwinlet - Qfil)/Qwinlet) \times ((Qdial + Qfil)/Qdial)\right]^{1/\gamma soln}$$

$$\gamma_{soln} = \exp\left(Qfil/(K0_{soln}) \times S\right) - 1$$

$$Qfil = Qpbp + Qpre + Qpost + Qpfr + Qanc$$

$$Qwinlet = Qpwinlet + (\beta kin_{soln} \times \alpha_{soln} \times Qrbcwinlet)$$

$$Qpwinlet = Qpw + Qpbp + Qpre + Qanc = Fp \times (1 - Hct) \times Qb + Qpbp + Qpre + Qanc$$

$$Qrbcwinlet = Qrbcw = Frbc \times Qrbc = Frbc \times Hct \times Qb$$

wherein $K0_{soln}$ diffusive mass transfer coefficient for solute n for the treatment unit;

S treatment unit filter surface area;

$\alpha_{soln}$ distribution coefficient of solute n between plasma water and red blood cells (RBC);

$\beta kin_{soln}$ empirical parameter defining the fraction of RBC water volume to consider in mass transfer computations for solute n (dependent on solute kinetics across RBC membrane);

Fp plasma water volume fraction;

Frbc intra erythrocyte water volume fraction;

Hct hematocrit;

Qfil filtration flow rate;

Qpbp flow rate of fluid crossing pre-blood pump line;

Qpre flow rate of fluid crossing pre-infusion line;

Qanc flow rate of fluid crossing ancillary line;

Qdial flow rate of fluid crossing the dialysis line;

Qb blood flow rate;

Qwinlet filter inlet water flow rate;

Qrbcw red blood cells water flow rate;

Qpw plasma water flow rate.

The diffusive mass transfer coefficient for solute n "$K0^{soln}$" is specific to each filter membrane—solute combination. The filter type of the treatment unit may be known to the control unit and the product "$K0_{soln}\times S$" may be a value embedded in the control unit. For instance, data of the filter type may be automatically identified by the control unit once the filter is installed or may be entered through a query to the user.

In a 22nd aspect according to aspect 16, the control unit is programmed to compute, or the method comprises computing, the clearance through the following approximation (simplified equation):

$$K_{sol} = Qfil + Qdial$$

wherein $K_{sol}$ clearance;

Qfil filtration flow rate;

Qdial flow rate of the fluid crossing the dialysis line.

In a 23rd aspect according to any of aspects 15 to 21, the control unit is programmed to compute, or the method comprises computing, a concentration of the selected solute at an inlet of the treatment unit from the patient parameter and to compute the rate of the selected solute leaving blood as a function of the concentration of the selected solute at an inlet of the treatment unit.

In a 24th aspect according to aspect 23, the control unit is programmed to compute, or the method comprises computing, the rate of the at least one selected solute leaving blood, or of each selected solute leaving blood, using the following equation:

$$Jeff_{soln} = Qdial \times Cdial_{soln} + K_{soln} \times (\text{Cpw\_inlet}_{soln} - Cdial_{soln}) + Qfil \times Cdial_{soln}$$

wherein $Jeff_{soln}$ rate of the selected solute n leaving blood;

Qdial flow rate of the fluid crossing the dialysis line;

$Cdial_{soln}$ concentration of selected solute n in dialysis line;

$K_{soln}$ clearance of solute n;

Qfil filtration flow rate;

$\text{Cpw\_inlet}_{soln}$ concentration of selected solute n at the inlet of the treatment unit (plasma water concentration).

In a 25th aspect according to aspect 23 or 24, the concentration of selected solute at the inlet of the treatment unit is function of the concentration of the selected solute n in patient's blood.

In a 26th aspect according to aspect 23 or 24 or 25, the control unit is programmed to compute, or the method comprises computing, the concentration of selected solute at the inlet of the treatment unit using the following equation:

$$\text{Cpw\_inlet}_{soln} = (Qw \times Cpw_{soln} + Qpbp \times Cpbp_{soln} + Qpre \times Cpre_{soln} + Qanc \times Canc_{soln}) / (Qwinlet)$$

wherein $$Qw = Qpw + \beta kin_{soln} \times \alpha_{soln} \times Qrbcw = [Fp \times (1 - Hct) + \beta kin_{soln} \times \alpha_{soln} \times Frbc \times Hct] \times Qb$$

$$Qwinlet = Qpwinlet + (\beta kin_{soln} \times \alpha_{soln} \times Qrbcwinlet)$$

$$Qpwinlet = Qpw + Qpbp + Qpre + Qanc = Fp \times (1 - Hct) \times Qb + Qpbp + Qpre + Qanc$$

$$Qrbcwinlet = Qrbcw = Frbc \times Qrbc = Frbc \times Hct \times Qb$$

wherein $\text{Cpw\_inlet}_{soln}$ concentration of selected solute n at the inlet of the treatment unit (plasma water concentration);

$\alpha_{soln}$ distribution coefficient of solute n between plasma water and red blood cells (RBC);

$\beta kin_{soln}$ empirical parameter defining the fraction of RBC water volume to consider in mass transfer computations for solute n (dependent on solute kinetics across RBC membrane);

Fp plasma water volume fraction;

Frbc intra erythrocyte water volume fraction;

Hct hematocrit;

$Cpbp_{soln}$ concentration of selected solute n in pre-blood pump line;

$Cpre_{soln}$in concentration of selected solute n in pre-infusion line;

$Canc_{soln}$ concentration of selected solute n in ancillary line;

Qpbp flow rate of fluid crossing pre-blood pump line;

Qpre flow rate of fluid crossing pre-infusion line;

Qanc flow rate of fluid crossing ancillary line;

Qb blood flow rate;

$Cpw_{soln}$ patient solute concentration of the selected solute n in patient's blood (plasma water concentration).

In a 27th aspect according to any of aspects 4 to 26 when according to aspect 3, the control unit is programmed to receive, or the method comprises receiving, the patient parameter/s through the interface.

In a 28th aspect according to any of aspects 1 to 27, the control unit is operatively connected or connectable to a device configured to measure and/or store the patient parameter/s; the control unit being configured to receive the patient parameter/s from said device.

In a 29th aspect according to aspect 28, the device configured to measure and/or store the patient parameter/s is an on-line monitoring device or an analyzer, such as a blood gas analyzer or an Electronical Medical Record (EMR) system of a hospital.

In a 30th aspect according to aspect 29, the apparatus for extracorporeal blood treatment comprises said device configured to measure and/or store the patient parameter/s.

In a 31st aspect according to any of aspects 27 to 30, the parameter concentration blood may be the plasma patient solute concentration or the plasma water patient solute concentration and the control unit is programmed to receive, or the method comprises receiving, the plasma patient solute concentration and to calculate the plasma water patient solute concentration.

In a $32^{nd}$ aspect according to any of aspects 1 to 31, the patient parameter is measured, estimated, or set.

In a $33^{rd}$ aspect according to any of aspects 1 to 32, the at least one selected solute comprises citrate and/or glucose and/or lactate and/or other metabolites like carbohydrates, protein peptides, ketone bodies, amino acids, triglycerides.

In a $34^{th}$ aspect according to aspect 33, the concentration of glucose in patient's blood is correlated to the energy balance through a table or chart.

In a $35^{th}$ aspect according to aspect 33, the concentration of citrate in patient's blood is set equal to zero or estimated as a steady state patient citrate concentration.

In a $36^{th}$ aspect according to aspect 33, the mass balance of citrate is computed assuming a steady state of patient citrate concentration.

In a $37^{th}$ aspect according to aspect 36, the control unit is programmed to compute, or the method comprises computing, the mass balance rate of citrate using the equations of aspects 14 and 24 together with the following equations:

$$J_{cit} = Cp_{cit} \times K_{cit\_met}$$

$$Qp \times Cp_{cit} + Qpbp \times Cpbp_{cit} + Qpre \times Cpre_{cit} = Qpwinlet \times \text{Cpw\_inlet}_{cit}$$

wherein

Qp plasma flow rate

Qpwinletplasma water flow rate at treatment unit inlet $Cp_{cit}$ patient plasma systemic citrate concentration $K_{cit\_met}$ patient citrate metabolic clearance In a $38^{th}$ aspect according to aspect 33, the concentration of lactate in patient's blood is correlated to the energy balance through a table or chart.

In a $39^{th}$ aspect according to any of aspects 1 to 36, each infusion line is connected to a respective source of fluid.

In a $40^{th}$ aspect according to any of aspects 1 to 39, said at least one fluid comprises a dialysis fluid and/or a replacement fluid and/or an anticoagulant solution, like citrate or heparin.

In a $41^{st}$ aspect according to any of aspects 1 to 40, the apparatus for extracorporeal blood treatment is a continuous renal replacement therapy (CRRT) apparatus.

In a $42^{nd}$ aspect according to aspect 41, the CRRT apparatus is configured to deliver various therapies, like CCVH, CWHDF, SCUF.

In a $43^{rd}$ aspect according to any of aspects 1 to 42, the apparatus for extracorporeal blood treatment is configured to apply Regional Citrate Anticoagulation (RCA).

In a $44^{th}$ aspect according to aspect 43, Regional Citrate Anticoagulation (RCA) is applied using an Anticoagulant Citrate Dextrose Solution, Solution A (ACD-A).

In a $45^{th}$ aspect according to any of aspects 1 to 43, the control unit is programmed to compute, or the method comprises computing, a caloric balance (load or loss) over a given time, e.g. a daily caloric balance, by integrating the energy balance over said given time.

Further characteristics of the present invention will better emerge from the detailed description that follows of some embodiments of the invention, illustrated by way of non-limiting examples in the accompanying figures.

DESCRIPTION OF THE DRAWINGS

The description will now follow, with reference to the appended Figures, provided by way of non-limiting example, in which:

FIG. 2 is a flow diagram of a method for calculating caloric balance according to the invention.

DETAILED DESCRIPTION

Figure 1:
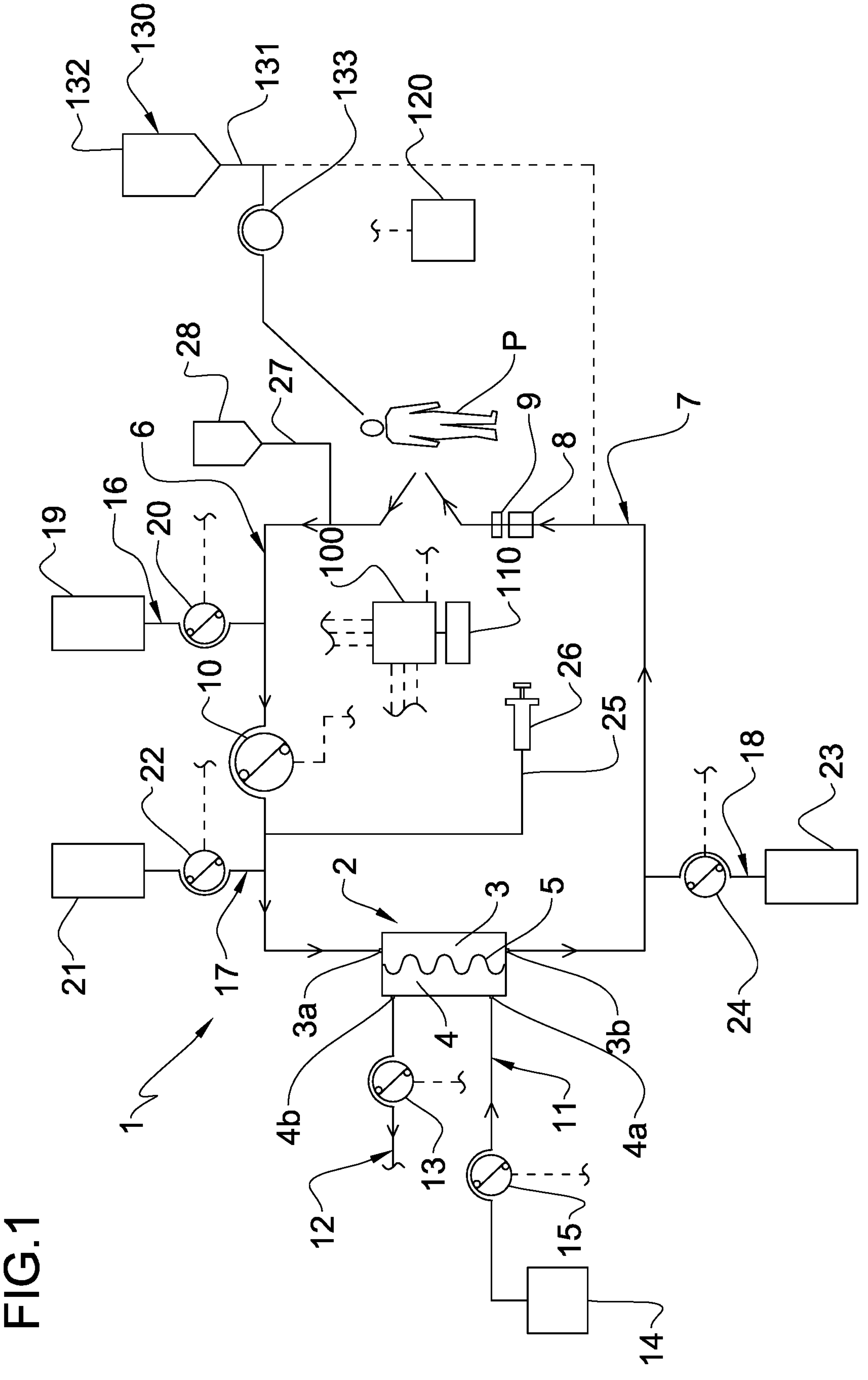
FIG. 1 schematically shows an extracorporeal blood treatment apparatus according to the invention.

An apparatus 1 for extracorporeal blood treatment is schematically represented in FIG. 1. The apparatus 1 may be a continuous renal replacement therapy (CRRT) apparatus configured to deliver various therapies, like CCVH, CVVHDF, SCUF. The apparatus 1 comprises a treatment or filtration unit 2 having a primary chamber 3 and a secondary chamber 4 separated by a semi-permeable membrane 5. Depending upon the treatment, the semi-permeable membrane 5 of the treatment unit 2 may be selected to have different properties and performances.

A blood circuit is coupled to the primary chamber 3 of the treatment unit 2. The blood circuit comprises a blood removal line 6 connected to an inlet 3*a* of the primary chamber 3, a blood return line 7 connected to an outlet 3*b* of the primary chamber 3. The blood removal line 6 and blood return line 7 are configured for connection to a cardiovascular system of a patient "P".

In use, the blood removal line 6 and the blood return line 7 are connected to a needle or to a catheter or other access device which is then placed in fluid communication with the patient "P" vascular system, such that blood may be withdrawn through the blood removal line 6, flown through the primary chamber 3 and then returned to the patient's vascular system through the blood return line 7. An air separator, such as a deaeration chamber 8, may be present on the blood return line 7. Moreover, a monitor valve 9 may be present on the blood return line 7, downstream the deaeration chamber 8. The blood flow through the blood circuit is controlled by a blood pump 10, for instance a peristaltic blood pump, acting either on the blood removal line 6 or on the blood return line 7. The embodiment of FIG. 1 shows the blood pump 10 coupled to a pump section of the blood removal line 6.

A dialysis circuit is connected to the secondary chamber 4 of the filtration unit 2 and comprises a dialysis line 11 connected to an inlet 4*a* of the secondary chamber 4 and an effluent line 12 connected to an outlet 4*b* of the secondary chamber 4 and to a drain, not shown. An effluent pump 13 is located on the effluent line 12 and is able to recall fluid from the second chamber 4. The dialysis line 11 is connected to a source 14, e.g. a bag or a preparation device, of fresh dialysis fluid and a dialysis pump 15 is located on the dialysis line 11 and is able to pump fluid to the second chamber 4. The apparatus 1 further comprises an infusion circuit comprising at least one infusion line. The infusion circuit shown in the embodiment of FIG. 1 comprises a pre-blood pump line 16, a pre-infusion line 17 and a post-infusion line 18. The pre-blood pump line 16 is connected to the blood removal line 6 upstream of the blood pump 10 and to a first source 19 of infusion fluid, e.g. a bag. A pre-blood pump 20 is located on the pre-blood pump line 16 and is able to pump fluid from the first source 19 to the blood circuit. The pre-infusion line 17 is connected to the blood removal line 6 downstream of the blood pump 10 and upstream of the treatment unit 2 and to a second source 21 of infusion fluid, e.g. a bag. A pre-infusion pump 22 is located on the pre-infusion line 17 and is able to pump fluid from the second source 21 to the blood circuit.

The post-infusion line 18 is connected to the blood return line 7 downstream of the treatment unit 2 and to a third source 23 of infusion fluid, e.g. a bag. A post-infusion pump 24 is located on the post-infusion line 18 and is able to pump fluid from the third source 23 to the blood circuit.

The infusion circuit may further comprises two ancillary infusion lines: i.e. a heparin line 25 with a syringe 26 and a citrate line 27 with a citrate bag 28. These two ancillary lines have been represented both in the schematic drawing of FIG. 1 together with all the other infusion lines, but, as detailed in the following, will be used according to the kind of treatment performed. Indeed, some treatments may require only citrate anticoagulation or only heparin anticoagulation and the other line may be absent or removed. In certain specific treatment without any anticoagulation, the two ancillary lines may be both absent.

A control unit 100 is connected and controls the blood pump 10, the effluent pump 13, the dialysis pump 15, the pre-blood pump 20, the pre-infusion pump 22 and the post-infusion pump 24 to regulate a blood flow rate "Qb" in the blood circuit, a fluid flow rate "Qdial" crossing the dialysis line 11, a fluid flow rate "Qeff" crossing the effluent line 12, a fluid flow rate "Qpbp" crossing the pre-blood pump line 16, a fluid flow rate "Qpre" crossing the pre-infusion line 17, a fluid flow rate "Qpost" crossing the post-infusion line 18. The control unit 100 may also control the syringe 26 and/or a pump on the citrate line 27 to control a supply and a flow rate "Qanc" of the ancillary fluid, like heparin and/or citrate solution. Through the control of the fluid flow rate "Qdial" crossing the dialysis line 11 and/or of the fluid flow rate "Qeff" crossing the effluent line 12, the control unit 100 is also configured to control/regulate a filtration flow rate "Qfil" in the treatment unit 2 and/or a patient fluid removal rate "Qpfr". Flow rate sensors, not shown, may be placed on the infusion lines and connected to the control unit 100 to better control the supply and flow rates of fluids.

The control unit 100 may be an electronic control unit comprising at least a CPU, a memory and input/output devices.

The control unit 100 comprises or is connected to an interface 110 configured to display data and/or allow a user to input data. For instance, the interface comprises a display, e.g. a touch screen, and/or buttons or a keyboard.

The dialysis fluid and the infusion fluids may contain solutes having energy/caloric load and the control unit 100 is able to evaluate, during the treatment, the exchange of energy/caloric load to/from the patient "P" due to said solutes.

Said solutes may comprise any solute having energy/caloric load, for instance citrate and/or glucose and/or lactate and/or other metabolites like protein peptides, ketone bodies, amino acids, triglycerides.

The infusion fluids may comprise replacement fluids and/or anticoagulant solutions, like citrate or heparin.

The energy/caloric balance (load or loss) may be displayed by the interface 110 to help the clinical staff to take responsibility of the effects of said balance imposed by the treatment.

The energy/caloric balance may also be used to perform further automatic controls of the apparatus 1.

For instance, the apparatus comprises an administering device 130 configured to administer nutritional products to the patient P during the treatment. Such administering device 130 comprises a nutritional line 131 having a first end in fluid communication with the nutritional bag 132 and a second end for infusing the nutritional products (e.g. as a nutritional solution) into either the blood return line 7 or directly into the patient vascular system. An infusion pump 133 is coupled to the nutritional line 131 to deliver the nutritional products.

The control unit 100 is connected to the infusion pump 133 and is configured to control the infusion pump 133 as a function also of the computed energy/caloric balance, in order to deliver a correct amount of nutritional products. This way, the amount of nutritional products administered to the patient P takes into account also the computed energy/caloric load coming from the solutes.

The control unit may also be connected to a Clinical Decision Support (CDS—not shown in the drawings) dealing with nutrition aspects installed on a computer and the computer is connected to an administering device configured to administer nutritional products to the patient comprising a nutritional line and an infusion pump coupled to the nutritional line. The CDS is configured to control the infusion pump as a function also of the computed energy balance.

Furthermore, the control unit 100 may be programmed to compute a caloric balance over a given time, e.g. a daily caloric balance, by integrating the energy balance over said given time.

Equations

In order to calculate the exchange of energy/caloric load, the control unit 100 is configured/programmed to receive the following data.

Prescription parameters of the extracorporeal blood treatment:

- blood flow rate "Qb";
- flow rate "Qpbp" of fluid crossing the pre-blood pump line 16;
- flow rate "Qpre" of fluid crossing the pre-infusion line 17;
- flow rate "Qpost" of fluid crossing the post-infusion line 18;
- flow rate "Qdial" of fluid crossing the dialysis line 11;
- flow rate "Qanc" of fluid crossing the ancillary line or lines 25, 27;
- filtration flow rate "Qfil" or patient fluid removal rate "Qpfr".

Solute concentrations of selected solute or solutes (e.g. Citrate, Glucose, Lactate) in the dialysis fluid and/or in the infusion fluids, e.g.:

- $Cpbp^{soln}$ concentration of selected solute n in pre-blood pump line;
- $Cpre_{soln}$in concentration of selected solute n in pre-infusion line;
- $Cpost_{soln}$ concentration of selected solute n in post-infusion line;
- $Canc_{soln}$ concentration of selected solute n in ancillary line;
- $Cdial_{soln}$ concentration of selected solute n in dialysis line.

Specific energy load "$Emet_{soln}$" of each selected solute (e.g. Citrate, Glucose, Lactate).

Patient data:

- concentration of the selected solute/s (e.g. Citrate, Glucose, Lactate) in patient's blood ("$Cp_{soln}$" plasma solute concentration or "$Cpw_{soln}$" plasma water solute concentration);
- patient body weight "BW";
- hematocrit "Hct".

Further data:

- $\alpha_{soln}$ distribution coefficient of solute n between plasma water and red blood cells (RBC);

$\beta kin_{soln}$ empirical parameter defining the fraction of RBC water volume to consider in mass transfer computations for solute n (dependent on solute kinetics across RBC membrane);

Fp=0.95 plasma water volume fraction (constant);

Frbc=0.85 intra erythrocyte water volume fraction (constant);

$K0_{soln}$ diffusive mass transfer coefficient for solute n for the treatment unit (specific to each filter membrane—solute combination);

S treatment unit filter surface area.

Said data may be entered through the interface 110 by the clinical staff or transmitted to the control unit 100 from a database part of the apparatus 1 or a remote database connected to the apparatus 1.

The control unit 100 is programmed/configured to compute a clearance "$K_{soln}$" of each "filter membrane—solute" combination through the following equation:

$$K_{soln} = [(Qwinlet \times Qdial) - (f_{soln} \times (Qwinlet - Qfil) \times (Qdial + Qfil))]/[Qdial - f_{soln} \times (Qwinlet - Qfil)] \quad (1)$$

wherein $$f_{soln} = \left[\left((Qwinlet - Qfil)/Qwinlet\right) \times \left((Qdia1 + Qfil)/Qdial\right)\right]^{1/\gamma soln}$$

$$\gamma_{soln} = \exp\left(Qfil/(K0_{soln}) \times S\right) - 1$$

$$Qwinlet = Qpwinlet + (\beta kin_{soln} \times \alpha_{soln} \times Qrbcwinlet)$$

$$Qpwinlet = Qpw + Qpbp + Qpre + Qanc = Fp \times (1 - Hct) \times Qb + Qpbp + Qpre + Qanc$$

$$Qrbcwinlet = Qrbcw = Frbc \times Qrbc = Frbc \times Hct \times Qb$$

Because previous equation (1) for solute clearance requires knowledge of the specific mass transfer coefficient (or resistance) and that this parameter may not be known, the following approximation of the solute clearance may be considered, in particular in the CRRT context:

$$K_{sol} = Qfil + Qdial \quad (2)$$

This simplified equation is generally an overestimate of the actual clearance.

The control unit 100 is programmed/configured to compute the water flow rate "Qw" matching with solute distribution volume considered for a given solute "n" through the following equation:

$$Qw = [Fp \times (1 - Hct) + \beta kin_{soln} \times \alpha_{soln} \times Frbc \times Hct] \times Qb \quad (3)$$

The control unit 100 is programmed/configured to compute the water flow rate "Qwinlet", matching with solute distribution volume considered for a given solute "n", at the inlet of the treatment unit 2 through the following equation:

$$Qwinlet = Fp \times (1 - Hct) \times Qb + Qpbp + Qpre + Qanc + (\beta kin_{soln} \times \alpha_{soln} \times Frbc \times Hct \times Qb) \quad (4)$$

The control unit 100 is programmed/configured to compute a concentration "Cpw_inletsoin" of each selected solute "n" at the inlet of the treatment unit 2 (plasma water concentration) through the following equation:

$$Cpw\_inlet_{soln} = (Qw \times Cpw_{soln} + Qpbp \times Cpbp_{soln} + Qpre \times Cpre_{soln} + Qanc \times Canc_{soln})/(Qwinlet) \quad (5)$$

wherein

Qw is calculated with equation (3);

Qwinlet is calculated with equation (4);

$Cpw_{soln}$ is the patient solute plasma water concentration.

The control unit 100 is programmed/configured to compute the rate "Jinfsoin" (e.g. in mmol per hour) of each selected solute "n" entering blood and the rate "$Jeff_{soln}$" of each selected solute "n" leaving blood through the following equations:

$$Jinf_{soln} = Qpbp \times Cpbp_{soln} + Qpre \times Cpre_{soln} + Qpost \times Cpost_{soln} + Qanc \times Canc_{soln} \quad (6)$$

$$Jeff_{soln} = Qdial \times Cdial_{soln} + K_{soln} \times (Cpw\_inlet_{soln} - Cdial_{soln}) + Qfil \times Cdial_{soln} \quad (7)$$

wherein $K_{soln}$ is calculated with equation (1) or (2);

$Cpw\_inlet_{soln}$ is calculated with equation (5).

The control unit 100 is programmed/configured to compute the mass balance rate of each selected solute through the following equation:

$$J_{soln} = Jinf_{soln} - Jeff_{soln} \quad (8)$$

wherein $Jinf_{soln}$ is calculated with equation (6);

$Jeff_{soln}$ is calculated with equation (7);

wherein $J_{soln}>0$ is for solute added to patient; and $J_{soln}<0$ is for solute removed from the patient.

The control unit 100 is programmed/configured to compute the overall energy balance using the following equation:

$$E = \sum E_{soln} = \sum J_{soln} \times Emet_{soln} \quad (9)$$

wherein $E_{soln}$ energy balance of each selected solute "n";

$J_{soln}$ mass balance rate of each selected solute "n" calculated from equation (8);

$Emet_{soln}$ specific energy load of each selected solute "n".

Patient Solute Concentration

As to compute the mass transfer of each selected solute from the blood to the effluent (equations 5 and 7), the model requires the solute concentration "$Cpw_{soln}$" in the patient venous blood pumped into the blood circuit.

This concentration may come from a measurement of the patient solute concentration "$Cp_{soln}$" that might be manually transferred to the control unit 100 (e.g. via a query from the user interface 110) or automatically transferred through digital connectivity between the apparatus 1 and a device 120 (schematically shown in FIG. 1) configured to measure and/or store the patient solute/s concentration/s.

Such device 120 may be an on-line monitoring device or an analyzer, such as a blood gas analyzer, or an Electronical Medical Record (EMR) system of a hospital. Other alternatives may be an apparatus 1 embedding an on-line monitoring device or having the capability to periodically produce blood/plasma samples to an integrated measurement device. However, above option may not be always possible (e.g. for citrate) and shall this be backed up with assumptions specific to each solute.

Patient Glucose Concentration

The blood glucose concentration is physiologically controlled in a relatively narrow range (baseline 3.9-6.1 mM) and increases significantly after meals (up to 7.8 mM in healthy individuals). Both hypo-glycemia and hyper-glycemia lead to various systemic symptoms.

In this context, display of a caloric load estimate without the knowledge of patient glucose concentration maybe strongly misleading. In the situation where no patient data is available to the system, an option is to report the dependence of caloric on patient glycemia, as a table or chart (see following example A4).

Patient Citrate Concentration

Citrate is usually not part of standard patient monitoring and its measurement technique is available only to few hospitals. The cited options to access patient blood concentration seems not valid in this case.

However, baseline blood citrate concentration is virtually zero in healthy subjects (i.e. about 0.1 mM) and in ICU patient not receiving blood extracorporeal therapies using citrate anticoagulation (RCA). It may reach levels of about 0.5 mM for patients under CRRT with RCA, and exceptionally values in the 0.5-1 mM range.

A simple assumption for citrate is thus to consider zero patient citrate concentration for estimating the caloric load.

A better way is to integrate in the model a simple estimate of the steady state patient citrate concentration assuming a "normal" metabolic clearance. Related specific equations are reported below.

Following equation (10) is the expression of patient (plasma) systemic citrate concentration at steady state.

$$J_{cit} = Cp_{cit} \times K_{cit\_met} \text{ or } Cp_{cit} = J_{cit}/K_{cit\_met} \tag{10}$$

wherein $K_{cit\_met}$ patient citrate metabolic clearance $Cp_{cit}$ patient plasma systemic citrate concentration Patient citrate metabolic clearance may be estimated=700×BW/72.

Considering Qanc=0, previous Equation (8) for citrate becomes:

$$J_{cit} = (Qpbp \times Cpbp_{cit} + Qpre \times Cpre_{cit} + Qpost \times Cpost_{cit}) - (Qdial \times Cdial_{cit} + K_{cit} \times (\text{Cpw\_inlet}_{cit} - Cdial_{cit}) + Qfil \times Cdial_{cit}) \tag{11}$$

The expression of citrate plasma water concentration at the inlet of the treatment unit 2 is as follows:

$$Qp \times Cp_{cit} + Qpbp \times Cpbp_{cit} + Qpre \times Cpre_{cit} = Qpwinlet \times \text{Cpw\_inlet}_{cit} \tag{12}$$

wherein

Qp plasma flow rate

Qpwinletplasma water flow rate at treatment unit inlet $Cp_{cit}$ patient plasma systemic citrate concentration therefore $$\text{Cpw\_inlet}_{cit} = (Qp \times Cp_{cit} + Qpbp \times Cpbp_{cit} + Qpre \times Cpre_{cit})/Qpwinlet$$

and $$J_{cit} = (Qpbp \times Cpbp_{cit} + Qpre \times Cpre_{cit} + Qpost \times Cpost_{cit}) - \left(Qdial \times Cdial_{cit} + K_{cit} \times \left(\left((Qp \times Cp_{cit} + Qpbp \times Cpbp_{cit} + Qpre \times Cpre_{cit})/Qpwinlet\right) - Cdial_{cit}\right) + Qfil \times Cdial_{cit}\right) \tag{13}$$

$$J_{cit} = \left[(Qpbp \times Cpbp_{cit} + Qpre \times Cpre_{cit}) \times \left(1 - K_{cit}/Qpwinlet\right) + (Qpost \times Cpost_{cit}) + (K_{cit} - Qfil - Qdial) \times Cdial_{cit}\right] / \left[1 + \left(K_{cit}/K_{cit\_met}\right) \times \left(Qp/Qpwinlet\right)\right] \tag{14}$$

Patient Lactate Concentration

In healthy subjects, baseline plasma lactate concentration is about 1±0.5 mM and will significantly increase with exercising.

In ICU patients, plasma lactate may significantly increase above physiologic levels in some clinical situations, e.g. septic shock.

Thus, the context is relatively similar to the case of glucose in case no lactate measurement data are provided to the system. In order to prevent misleading information, caloric load shall be reported over a range of lactate concentrations, either in the format of a table or of a chart.

Another general aspect of the patient solute concentration is that the plasma concentration "$Cp_{soln}$" will be typically measured, while the described equations (e.g. Equation 5) refer to plasma water concentration "$Cpw_{soln}$". Correction for the volume fraction of proteins (Fp) shall be performed, either assuming a default value or as a function of total proteins concentration in plasma.

EXAMPLES

A CRRT apparatus 1 is considered and the following Table 1 contains definition and notations for the CRRT flows and fluids composition.

TABLE 1

| Circuit ID | Short description | Flow rate | Solute concentrations |
|---|---|---|---|
| Pbp | Pre-blood pump infusion | Qpbp | $Cpbp_{glu}$, $Cpbp_{cit}$, $Cpbp_{lac}$ |
| Pre | Pre-filter infusion | Qpre | $Cpre_{glu}$, $Cpre_{cit}$, $Cpre_{lac}$ |
| Post | Post-filter infusion | Qpost | $Cpost_{glu}$, $Cpost_{cit}$, $Cpost_{lac}$ |
| Dial | Dialysis circuit | Qdial | $Cdial_{glu}$, $Cdial_{cit}$, $Cdial_{lac}$ |

The solutes considered are Glucose, Citrate and Lactate, since are those having significant specific energy contribution, defined as the amount of energy produced when metabolized, significant concentration in the patient or in the CRRT fluids, significant mass transfer along the CRRT process.

Modelling parameters for the selected solutes are reported in the following Tables 2, 3 and 4.

TABLE 2

| Glucose | | |
|---|---|---|
| Parameter | Unit | Value |
| mw | g/mol | 180.0 |
| $K0_{glu} \times S$ | ml/min | 200 |
| $\beta kin_{glu}$ | dimensionless | 0 |
| $\alpha_{glu}$ | dimensionless | 0.8 |
| $Emet_{glu}$ | kJ/mmol | 2.83 |

TABLE 3

| Citrate | | |
|---|---|---|
| Parameter | Unit | Value |
| mw | g/mol | — |
| $K0_{cit} \times S$ | ml/min | 109 |
| $\beta kin_{cit}$ | dimensionless | 0 |
| $\alpha_{cit}$ | dimensionless | — |
| $Emet_{cit}$ | kJ/mmol | 0.66 |

TABLE 4

| Lactate | | |
|---|---|---|
| Parameter | Unit | Value |
| mw | g/mol | 89 |
| $K0_{lac} \times S$ | ml/min | 264 |
| $\beta kin_{lac}$ | dimensionless | 0 |
| $\alpha_{lac}$ | dimensionless | 0.5 |
| $Emet_{lac}$ | kJ/mmol | 1.36 |

Examples A: Citrate Anticoagulation Using ACD-A Solution

Set of examples "A" is built around a citrate anticoagulation prescription using ACD-A (Anticoagulant Citrate Dextrose Solution, Solution A) as anticoagulant solution; according to high glucose content of the ACD-A solution all other fluids are assumed to be free of glucose. This series of example also consider the use of lactate containing fluids (replacement and dialysate).

The composition of fluids is in the following Table 5.

TABLE 5

| Fluid circuit | pbp | pre | post | dial |
|---|---|---|---|---|
| Glucose (mM) | 124 | 0 | 0 | 0 |
| Citrate (mM) | 113 | 0 | 0 | 0 |
| Lactate (mM) | 0 | 3 | 3 | 3 |

Example A1—CWHDF Treatment Using ACD-A

TABLE 6

| Patient data | |
|---|---|
| BW (kg) | 80 |
| Hct (%) | 30 |
| $Cp_{glu}$(mM) | 4.8 |
| $Cp_{lac}$(mM) | 2.1 |

TABLE 7

| CRRT prescriptions | |
|---|---|
| Qb (ml/min) | 140 |
| Qpbp (ml/h) | 297 |
| Qpre (ml/h) | 0 |
| Qpost (ml/h) | 1000 |
| Qdial (ml/h) | 1000 |
| Qanc (ml/h) | 15 |
| Qpfr (ml/h) | 120 |

TABLE 8

| Computation results | | | | |
|---|---|---|---|---|
| Solute | Glucose | Citrate | Lactate | Overall energy balance E |
| $J_{soln}$ (mmol/h) | 10.0 | 19.1 | 0.9 | — |
| $E_{soln}$ (kJ/h) | 28.4 | 12.6 | 1.2 | 42.2 |

Example A2—Same as A1 with Patient Having High Glycemia

TABLE 9

| Patient data | |
|---|---|
| BW (kg) | 80 |
| Hct (%) | 30 |
| $Cp_{glu}$(mM) | 6.7 |
| $Cp_{lac}$(mM) | 1 |

TABLE 10

| Computation results | | | | |
|---|---|---|---|---|
| Solute | Glucose | Citrate | Lactate | Overall energy balance E |
| $J_{soln}$ (mmol/h) | 5.4 | 19.1 | 0.9 | — |
| $E_{soln}$ (kJ/h) | 15.3 | 12.6 | 1.2 | 29.2 |

Example A3—Same as A1 with Higher Dialysis Flow and CRRT Dose

TABLE 11

| CRRT prescriptions | |
|---|---|
| Qb (ml/min) | 140 |
| Qpbp (ml/h) | 297 |
| Qpre (ml/h) | 0 |
| Qpost (ml/h) | 1000 |
| Qdial (ml/h) | 2000 |
| Qanc (ml/h) | 15 |
| Qpfr (ml/h) | 120 |

TABLE 12

| Computation results | | | | |
|---|---|---|---|---|
| Solute | Glucose | Citrate | Lactate | Overall energy balance E |
| $J_{soln}$ (mmol/h) | 0.5 | 15.6 | 1.7 | — |
| $E_{soln}$ (kJ/h) | 1.5 | 10.3 | 2.4 | 14.2 |

Example A4—Same as A1 Except for Variable Patient Glucose Concentration

The dependence of caloric on patient glycemia is reported in the following table 12A.

TABLE 12A

| $Cp_{glu}$(mM) | E (kJ/h) |
|---|---|
| 2.5 | 58 |
| 3 | 54.6 |
| 3.5 | 51.1 |
| 4 | 47.7 |
| 4.5 | 44.3 |
| 5 | 40.8 |
| 5.5 | 37.4 |
| 6 | 34 |
| 6.5 | 30.5 |
| 7 | 27.1 |
| 7.5 | 23.7 |
| 8 | 20.3 |

Caloric load computed for first example A1 matches with more than 900 kJ/day assuming an effective therapy time of about 22 hours a day; such amount represents about 10% of the daily patient energy expenditure.

Examples A2, A3 and A4 illustrate the high sensitivity of the caloric load to both patient parameters (examples A2 and A4) or prescription parameters (example A3). In example A3 with an effluent dose of about 40 ml/kg/h, the caloric load is brought down to negligible levels (about 300 kJ/day). All A examples show a minimal contribution of lactate for a patient having a lactatemia moderately elevated in combination with solutions having a lactate concentration above the physiologic range.

Examples B: Citrate Anticoagulation Using a "Diluted" Citrate Solution

Set of examples "B" is built around a citrate anticoagulation prescription using a "diluted" citrate solution without glucose as anticoagulant solution. This series of example also consider the use of lactate-free fluids (replacement and dialysate). The composition of fluids is in the following Table 13.

TABLE 13

| Fluid circuit | pbp | pre | post | dial |
|---|---|---|---|---|
| Glucose (mM) | 0 | 0 | 6 | 6 |
| Citrate (mM) | 18 | 0 | 0 | 0 |
| Lactate (mM) | 0 | 0 | 0 | 0 |

Example B1—CVVHDF Treatment Using Diluted Citrate—Low Glycemia Range

TABLE 14

| Patient data | |
|---|---|
| BW (kg) | 65 |
| Hct (%) | 36 |
| $Cp_{glu}$(mM) | 3.5 |
| $Cp_{lac}$(mM) | 1.5 |

TABLE 15

| CRRT prescriptions | |
|---|---|
| Qb (ml/min) | 120 |
| Qpbp (ml/h) | 1320 |
| Qpre (ml/h) | 0 |
| Qpost (ml/h) | 250 |
| Qdial (ml/h) | 500 |
| Qanc (ml/h) | 0 |
| Qpfr (ml/h) | 90 |

TABLE 16

| Computation results | | | | |
|---|---|---|---|---|
| Solute | Glucose | Citrate | Lactate | Overall energy balance E |
| $J_{soln}$ (mmol/h) | −1.6 | 14.1 | −2.6 | — |
| $E_{soln}$ (kJ/h) | −4.6 | 9.3 | −3.6 | 1.2 |

Example B2—Same as B1 with High Glycemia Range

TABLE 17

| Patient data | |
|---|---|
| BW (kg) | 65 |
| Hct (%) | 36 |
| $Cp_{glu}$(mM) | 6.5 |
| $Cp_{lac}$(mM) | 1.5 |

TABLE 18

| Computation results | | | | |
|---|---|---|---|---|
| Solute | Glucose | Citrate | Lactate | Overall energy balance E |
| $J_{soln}$ (mmol/h) | −6.9 | 14.1 | −2.6 | — |
| $E_{soln}$ (kJ/h) | −19.4 | 9.3 | −3.6 | −13.6 |

Example B3—Same as B1 with Higher CRRT Dose

TABLE 19

| CRRT prescriptions | |
|---|---|
| Qb (ml/min) | 120 |
| Qpbp (ml/h) | 1320 |

TABLE 19-continued

| CRRT prescriptions | |
|---|---|
| Qpre (ml/h) | 0 |
| Qpost (ml/h) | 500 |
| Qdial (ml/h) | 750 |
| Qanc (ml/h) | 0 |
| Qpfr (ml/h) | 90 |

TABLE 20

| Computation results | | | | |
|---|---|---|---|---|
| Solute | Glucose | Citrate | Lactate | Overall energy balance E |
| $J_{soln}$ (mmol/h) | 0.0 | 12.2 | −3.2 | — |
| $E_{soln}$ (kJ/h) | −0.1 | 8.0 | −4.4 | 3.5 |

All “B” examples lead to caloric load rates which are fairly negligible with respect to patient energy expenditure.

B2 is an example of negative caloric load, meaning that the net impact of the CRRT therapy is a loss of energy via the loss of metabolites. B2 example considers use of glucose-containing dialysate and infusion fluids; in case glucose-free fluid would be used, caloric loss of example B2 would become 17.6 kJ/h, which remains somehow negligible versus patient overall metabolism.

Examples C: No Anticoagulation

Set of examples “C” is built for the circumstance of heparin or no anticoagulation where citrate is not present in any fluid.

These examples illustrate the effect of the glucose and lactate content of the fluids.

The composition of fluids for examples C1 and C2 is in the following Table 13.

TABLE 21

| Fluid circuit | pbp | pre | post | dial |
|---|---|---|---|---|
| Glucose (mM) | 0 | 6 | 6 | 6 |
| Citrate (mM) | 0 | 0 | 0 | 0 |
| Lactate (mM) | 0 | 3 | 3 | 3 |

Example C1—CVVH Treatment in Standard Anticoagulation/Glucose and Lactate Containing Fluids

TABLE 22

| Patient data | |
|---|---|
| BW (kg) | 95 |
| Hct (%) | 24 |
| $Cp_{glu}$(mM) | 4.0 |
| $Cp_{lac}$(mM) | 1.2 |

TABLE 23

| CRRT prescriptions | |
|---|---|
| Qb (ml/min) | 210 |
| Qpbp (ml/h) | 0 |
| Qpre (ml/h) | 1200 |
| Qpost (ml/h) | 1800 |
| Qdial (ml/h) | 0 |
| Qanc (ml/h) | 30 |
| Qpfr (ml/h) | 120 |

TABLE 24

| Computation results | | | | |
|---|---|---|---|---|
| Solute | Glucose | Citrate | Lactate | Overall energy balance E |
| $J_{soln}$ (mmol/h) | 4.1 | 0.0 | 4.4 | — |
| $E_{soln}$ (kJ/h) | 11.5 | 0.0 | 6.0 | 17.5 |

Example C1bis—Same as C1 with Unspecified Patient Lactate and Glucose Concentrations The dependence of caloric on patient lactate and glucose is reported in the following table 24bis.

TABLE 24bis

| $Cp_{lac}$(mM) | $Cp_{glu}$(mM) = 6 E (kJ/h) | $Cp_{glu}$(mM) = 4 E (kJ/h) | $Cp_{glu}$(mM) = 2 E (kJ/h) |
|---|---|---|---|
| 0 | 5.7 | 22.3 | 38.9 |
| 0.5 | 3.7 | 20.3 | 36.9 |
| 1 | 1.7 | 18.3 | 34.9 |
| 1.5 | −0.3 | 16.3 | 32.9 |
| 2 | −2.3 | 14.3 | 30.9 |
| 2.5 | −4.3 | 12.3 | 28.9 |
| 3 | −6.2 | 10.3 | 26.9 |
| 3.5 | −8.2 | 8.3 | 24.9 |
| 4 | −10.2 | 6.4 | 22.9 |
| 4.5 | −12.2 | 4.4 | 20.9 |
| 5 | −14.2 | 2.4 | 18.9 |

Example C2—Same as C1 with Higher CRRT Dose

TABLE 25

| CRRT prescriptions | |
|---|---|
| Qb (ml/min) | 250 |
| Qpbp (ml/h) | 0 |
| Qpre (ml/h) | 2000 |
| Qpost (ml/h) | 2000 |
| Qdial (ml/h) | 0 |
| Qanc (ml/h) | 30 |
| Qpfr (ml/h) | 120 |

TABLE 26

| Computation results | | | | |
|---|---|---|---|---|
| Solute | Glucose | Citrate | Lactate | Overall energy balance E |
| $J_{soln}$ (mmol/h) | 5.4 | 0.0 | 5.6 | — |
| $E_{soln}$ (kJ/h) | 15.2 | 0.0 | 7.7 | 22.8 |

Example C3—Same as C1 with Glucose and Lactate-Free Fluids

The composition of fluids for example C3 is in the following Table 13.

TABLE 27

| Fluid circuit | pbp | pre | post | dial |
|---|---|---|---|---|
| Glucose (mM) | 0 | 6 | 6 | 6 |
| Citrate (mM) | 0 | 0 | 0 | 0 |
| Lactate (mM) | 0 | 3 | 3 | 3 |

TABLE 28

| Computation results | | | | |
|---|---|---|---|---|
| Solute | Glucose | Citrate | Lactate | Overall energy balance E |
| $J_{soln}$ (mmol/h) | −11.7 | 0.0 | −3.5 | — |
| $E_{soln}$ (kJ/h) | −33.2 | 0.0 | −4.8 | −38.0 |

Example C1 illustrates that a typical CRRT prescription without citrate anticoagulation leads to minor patient caloric load when using fluids having glucose and lactate concentrations in the high range of physiologic values (and beyond for lactate), when the patient has both 'normal' glucose and lactate levels.

In this prescription scenario, increase of the CRRT dose has a marginal effect on the caloric load.

On the other hand, use of glucose and lactate free fluids dramatically shifts the caloric load into the negative range, reaching caloric losses in the range of 10% of the baseline patient metabolism (about 840 kJ in example C3).

While the invention has been described in connection with what is presently considered to be the most practical and preferred embodiment, it is to be understood that the invention is not to be limited to the disclosed embodiment, but on the contrary, is intended to cover modifications included within the scope of the appended claims.

The invention claimed is:

1. An apparatus for extracorporeal blood treatment comprising:

- a treatment unit;
- a blood circuit coupled to the treatment unit and comprising a blood removal line and a blood return line configured to connect to a vascular system of a patient;
- a blood pump coupled to a pump section of the blood circuit;
- an effluent line connected to the treatment unit;
- at least one infusion line connected to the blood circuit and/or a dialysis line connected to the treatment unit;
- wherein the at least one infusion line and/or the dialysis line are connected to a source of a fluid;
- a control unit operably connected to the blood pump and configured to receive:
- a solute concentration of a selected solute in the fluid;
- a patient parameter related to a patient solute concentration of the selected solute in a patient's blood;
- a specific energy load of the selected solute;
- a measured or set fluid flow rate or rates of a fluid crossing the at least one infusion line and/or the dialysis line;
- a measured or set filtration flow rate in the treatment unit or a measured or set patient fluid removal rate;
- during the extracorporeal blood treatment, the control unit being configured to:
- compute a mass balance rate of the selected solute from the solute concentration, from the patient parameter, from the fluid flow rate or rates, and from the filtration flow rate or the patient fluid removal rate;
- compute, from the computed mass balance rate and from the specific energy load, an energy balance due to the selected solute during the extracorporeal blood treatment.

2. The apparatus of claim 1, wherein the patient parameter is the patient solute concentration.

3. The apparatus of claim 1, wherein the control unit is connected to an interface and is configured to display the computed energy balance through the interface.

4. The apparatus of claim 1, wherein the control unit is operably connected to an infusion pump for administering nutritional products to the patient and is configured to control the infusion pump as a function of the computed energy balance.

5. The apparatus of claim 1, comprising an administering device configured to administer nutritional products to the patient during the extracorporeal blood treatment; the administering device comprising a nutritional line and an infusion pump coupled to the nutritional line, the nutritional line being in fluid communication with a nutritional bag and with one or both of the blood return line and directly with the patient.

6. The apparatus of claim 5, wherein the control unit is operably connected to a support tool dealing with nutrition aspects installed on a computer; the computer being connected to the administering device; the support tool being configured to control the infusion pump as a function of the energy balance computed by the control unit.

7. The apparatus of claim 1, wherein the selected solute comprises a plurality of selected solutes, the control unit is configured to sum the energy balance of each of the selected solutes to obtain an overall energy balance due to the plurality of selected solutes.

8. The apparatus of claim 7, wherein computing the energy balance comprises:

- multiplying the mass balance rate of each selected solute of the plurality of selected solutes for the respective specific energy load to obtain an energy balance of each selected solute.

9. The apparatus of claim 1, comprising a plurality of sources of respective fluids, wherein computing the mass balance rate of the selected solute comprises computing the mass balance rate of the selected solute.

10. The apparatus of claim 1, wherein the control unit is configured to compute the mass balance rate of the selected solute as a difference between a rate of the selected solute entering blood and a rate of the selected solute leaving blood.

11. The apparatus of claim 10, wherein the control unit is configured to compute the rate of the selected solute entering blood as a function of the fluid flow rate of the fluid flowing in the at least one infusion line and of the solute concentration in the fluid.

12. The apparatus of claim 10, wherein the control unit is configured to compute the rate of the selected solute leaving blood as a function of the filtration flow rate and of the patient parameter.

13. The apparatus of claim 12, wherein the control unit is configured to compute the rate of the selected solute leaving blood as a function of the fluid flow rate of the fluid flowing in the dialysis line.

14. The apparatus of claim 12, wherein the control unit is configured to compute the rate of the selected solute leaving blood as a function of a clearance of the solute for the treatment unit.

15. The apparatus of claim 14, wherein the control unit is configured to compute the clearance from a diffusive mass transfer coefficient of the solute for the treatment unit.

16. The apparatus of claim 12, wherein the control unit is configured to compute a concentration of the selected solute at an inlet of the treatment unit from the patient parameter and to compute the rate of the selected solute leaving blood as a function of the concentration of the selected solute at the inlet of the treatment unit.

17. The apparatus of claim 12, comprising a device configured to measure or store one or more of the patient parameters and the control unit is configured to receive the one or more of the patient parameter from the device, wherein the device is configured to measure or store the one or more of the patient parameters in an on-line monitoring device or an analyzer and comprises a blood gas analyzer or an Electronical Medical Record system of a hospital.

18. The apparatus of claim 1, wherein the selected solute comprises citrate or glucose or lactate.

19. The apparatus of claim 18, wherein the concentration of glucose in patient's blood is correlated to the energy balance through a table or chart.

20. The apparatus of claim 18, wherein the concentration of citrate in patient's blood is set equal to zero or estimated as a steady state patient citrate concentration.

21. The apparatus of claim 18, wherein the concentration of lactate in patient's blood is correlated to the energy balance through a table or chart.

22. The apparatus of claim 1, wherein the at least one infusion line comprises: one or more of a pre-blood pump line, a pre-infusion line, a post-infusion line, and an ancillary infusion line; and the at least one fluid comprises a replacement fluid or an anticoagulant solution.

23. The apparatus of claim 1, wherein the apparatus for extracorporeal blood treatment is a continuous renal replacement therapy apparatus configured to apply Regional Citrate Anticoagulation.

24. The apparatus of claim 1, wherein the control unit is configured to compute a caloric balance over a given time by integrating the energy balance over the given time.

25. An apparatus for extracorporeal blood treatment comprising:
- a treatment unit;
- a blood circuit coupled to the treatment unit and comprising a blood removal line and a blood return line configured to connect to a vascular system of a patient;
- a blood pump coupled to a pump section of the blood circuit;
- an effluent line connected to the treatment unit;
- a dialysis line connected to the treatment unit;
- at least one infusion line connected to the blood circuit and comprising one or more of:
  - a pre-blood pump line;
  - a pre-infusion line;
  - a post-infusion line; and
  - an ancillary infusion line;

wherein the at least one infusion line and the dialysis line are connected to a source of a fluid;

a control unit operably connected to the blood pump and configured to compute a caloric balance over a given time by integrating an energy balance over the given time, the control unit being configured to receive:
- a solute concentration of a selected solute in the fluid, the selected solute comprising citrate or glucose or lactate;
- a patient solute concentration of the selected solute in patient's blood;
- a specific energy load of the selected solute;
- a measured or set fluid flow rate of a fluid flowing in the at least one infusion line;
- a measured or set fluid flow rate of a fluid flowing in the dialysis line;
- a measured or set filtration flow rate in the treatment unit or a measured or set patient fluid removal rate;

the control unit being configured to, during the extracorporeal blood treatment:
- compute a mass balance rate of the selected solute from the solute concentration, from
- the patient solute concentration,
- the fluid flow rate flowing in the at least one infusion line, and
- either the filtration flow rate or the patient fluid removal rate;
- compute, from the computed mass balance rate and from the specific energy load, the energy balance due to the selected solute during the extracorporeal blood treatment.

26. The apparatus of claim 25, wherein the control unit is configured to compute the energy balance using the following equation:

$$E_{soln} = J_{soln} \times Emet_{soln}$$

wherein $E_{soln}$ is the energy balance of selected solute n;

$J_{soln}$ is the mass balance rate of selected solute n;

$Emet_{soln}$ is the specific energy load of selected solute n;

wherein:

$J_{soln}>0$ is for solute added to patient; and $J_{soln}<0$ is for solute removed from the patient.

* * * * *